United States Patent [19]

Herzog et al.

[11] 4,055,570

[45] Oct. 25, 1977

[54] IMIDAZOLIDINE-4,5-DIONE DICARBOXYLIC ACIDS AND DERIVATIVES

[75] Inventors: Hans Herzog, Badenweiler; Lothar Buxbaum; Thomas Kainmüller, both of Lindenfels, Odenwald, all of Germany; Jürgen Habermeier, Pfeffingen, Switzerland

[73] Assignee: Ciba-Geigy Corporation, Ardsley, N.Y.

[21] Appl. No.: 676,850

[22] Filed: Apr. 14, 1976

[30] Foreign Application Priority Data

Apr. 23, 1975 Switzerland ........................ 5204/75
Feb. 12, 1976 Switzerland ........................ 1708/76

[51] Int. Cl.$^2$ ............................................. C07D 233/72
[52] U.S. Cl. .................................. 548/301; 260/47 C; 260/47 CZ; 548/302
[58] Field of Search ...................................... 260/309.7

[56] References Cited

U.S. PATENT DOCUMENTS

| 3,196,152 | 7/1965 | Wright et al. | 260/309.7 |
| 3,835,151 | 9/1974 | Havera et al. | 260/309.5 |
| 3,917,636 | 11/1975 | Cusic et al. | 260/309.5 |
| 3,917,637 | 11/1975 | Porret et al. | 260/309.5 |

OTHER PUBLICATIONS

Cassella Farbwerke Mainkur, Chem. Abst., 1956, vol. 50, column 5037.
Gruber et al., Chem. Abst., 1972, vol. 76, No. 34253u.
Kuenstler et al., Chem. Abst., 1972, vol. 76, No. 46206u.

Primary Examiner—Natalie Trousof
Attorney, Agent, or Firm—Luther A. R. Hall

[57] ABSTRACT

Dicarboxylic acids and dicarboxylic acid derivatives which contain N,N-imidazolidine-4,5-diones are useful monomers for the manufacture of polymers, in particular polyesters.

13 Claims, No Drawings

IMIDAZOLIDINE-4,5-DIONE DICARBOXYLIC ACIDS AND DERIVATIVES

The present invention provides new dicarboxylic acids and dicarboxylic acid derivatives which contain an imidazolidine-4,5-dione ring, and also a process for their manufacture.

Dicarboxylic acids which contain a N,N-heterocyclic radical in the molecule are already known. For example, "Chemical Abstracts", vol. 59, page 3907 (e), describes the manufacture of dicarboxylic acids which contain hydantoin and alkylene-bis-hydantoins by cyanoethylation of hydantoin and alkylene-bis-hydantoins and subsequent hydrolysis of the resultant cyanoethyl compounds to give dicarboxylic acids. However, these dicarboxylic acids have the disadvantage that they possess no great heat stability and during the further processing at elevated temperature, for example in the manufacture of polyesters by the melt condensation process, they dissociate readily into the hydantoin and acrylic compounds.

German Offenlegungsschrift No. 1,906,492 discloses the manufacture of oligo- and polyhydantoins which contain carboxylic acid functions by reacting polyglycine ester with isocyanates which contain carboxylic acid functions. The disadvantages of this process are that, on the one hand, the necessary starting materials are obtained only by means of complicated syntheses, and, on the other hand, that the reaction of the polyglycine esters with the isocyanates, which takes place with cyclisation, requires relatively high temperatures and the desired substances have to be separated from products which have not been cyclised quantitatively from the reaction mixture.

In the process disclosed in German Offenlegungsschrift No. 1,916,932 for the manufacture of dicarboxylic acid derivatives which contain the triketoimidazolidine ring from diisocyanates and N-(p-carboxyethylphenyl)-oxamic acid alkyl esters, the synthesis proceeds via a cyclisation reaction which can only be carried out to some extent satisfactorily in thin layers. Moreover, after this synthesis the dicarboxylic acids and their derivatives are not obtained in sufficient purity.

1,3-Bis-(3-methoxycarbonylphenyl)-4,5-dioxo-2-methylene-imidazolidine is described as a dicarboxylic acid which contains a vinyl group in Beilstein, 24,339. The dicarboxylic acid obtained by a special process by boiling oxanilide-dicarboxylic acid (3,3')-dimethyl ester with acetic anhydride and sodium acetate is, however, not suitable for obtaining linear polyesters by the melt condensation process at elevated temperatures on account of its unsaturated character, since secondary reactions can result in degradation and crosslinkings.

The present invention has for its object to provide dicarboxylic acids with acid amide groups that do not contain a hydrogen atom in this group and which are suitable for the manufacture of heat-resistant plastics.

The present invention therefore provides dicarboxylic acids and dicarboxylic acid derivatives which contain an imidazolidine-4,5-dione ring of the formula I

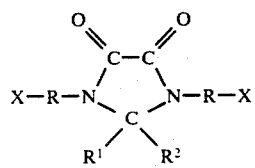

(I)

wherein
X represents nitrile, carboxyl, chlorocarbonyl, phenoxycarbonyl or alkoxycarbonyl containing 1 to 10 carbon atoms in the alkoxy moiety,
R represents unsubstituted or substituted alkylene containing 1 or 2 carbon atoms in the chain, cyclohexylene, phenylene or benzylene the methyl group of which is attached to the nitrogen atom,
each of $R^1$ and $R^2$ independently represents hydrogen, alkyl of 1 to 18 carbon atoms, cycloalkyl containing 5 to 8 ring members, phenyl, or together they represent tetramethylene, pentamethylene, hexamethylene or heptamethylene, with the proviso that, if R represents phenylene, $R^1$ is a hydrogen atom and $R^2$ is alkyl of 1 to 18 carbon atoms or cycloalkyl containing 5 to 8 ring members.

The alkoxy moiety of the alkoxycarbonyl group can be linear or branched and contains preferably 1 to 6, in particular 1 to 4, carbon atoms. Examples are propoxy, butoxy, isobutoxy, pentoxy, neopentoxy, hexoxy, octoxy, isooctoxy, decoxy and, in particular, methoxy or ethoxy.

X is preferably carboxyl, phenoxy, methoxy or ethoxycarbonyl.

Unsubstituted or substituted alkylene is in particular alkyl-substituted alkylene, the alkyl moiety preferably containing 1 to 6, in particular 1 or 2 carbon atoms.

Examples of R are: methylene, ethylidene, 1,1-propylidene, 2,2-propylidene, 1,1- or 2,2-butylidene, hexylidene, ethylene, 1,2-propylene, 1,2- or 2,3-butylene, 1,2-pentylene, 2,3-hexylene, 1,2- or 3,4-octylene, 5,6-decylene, 7,8-tetradecylene. Methylene, ethylidene and 1,4-benzylene are particularly preferred. Of the possible position isomers of cyclohexylene, phenylene and benzylene, the 1,4-derivatives are especially preferred.

Each of $R^1$ and $R^2$ can be linear or branched alkyl containing preferably 1 to 12, in particular 1 to 6, carbon atoms, and cycloalkyl containing preferably 5 or 6 ring members. $R^1$ and $R^2$ together represent preferably hexamethylene and, in particular, pentamethylene or tetramethylene.

Examples of $R^1$ and $R^2$ are: methyl, ethyl, propyl, butyl, isobutyl, pentyl, hexyl, octyl, isooctyl, decyl, dodecyl, tetradecyl, octadecyl.

Most preferably each of $R^1$ and $R^2$ is methyl, ethyl and hydrogen.

The dicarboxylic acids and dicarboxylic acid derivatives of the formula I, in which R is not phenylene, are obtained by reacting an imidazolidine-4,5-dione of the formula II

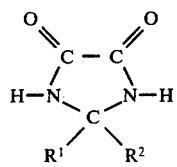

(II)

wherein $R^1$ and $R^2$ are as defined in formula I, or the disodium salts thereof, with a compound of the formula III $$Y - R - X$$ (III)

wherein R and X are as defined in formula I and Y represents chlorine or bromine, with hydrogen chloride or hydrogen bromide, or sodium chloride or sodium bromide, being split off.

The reaction is normally carried out in a polar aprotic solvent, such as dimethyl formamide, dimethyl acetamide, hexamethylphosphoric triamide or dioxan. It is also possible to carry out the reaction without a solvent, i.e. in the melt. As a rule, 1 mole of a chlorine-containing compound of the formula III, preferably a small excess thereof, is used per equivalent of reactive NH group in the starting product of formula II. The surplus can consist of molar amounts. The reaction, which takes place with dehydrohalogenation, is advantageously carried out in the presence of an acid acceptor, which is added to the solvent in at least equivalent amounts, referred to the calculated amount of liberated hydrogen halide. Suitable acid acceptors for this reaction are in particular ground anhydrous potassium or sodium carbonate. Sodium hydride, sodium ethylate or sodium methylate, or sodium hydroxide powder, are also suitable acid acceptors. The reaction is carried out at temperatures between 20° and 180° C, preferably between 50° and 150° C.

The reaction product is isolated by filtering the reaction mixture hot to remove the potassium halide which forms when using, for example, potassium carbonate as acid acceptor, and the desired product is obtained by letting it crystallise out from the reaction solution, or by pouring the reaction solution into water with subsequent precipitation, or by evaporating the reaction solution to dryness and recrystallising the crude product in an organic solvent. Various organic solvents are suitable for this purpose, for example methanol, ethanol or tetrahydrofuran.

When using the imidazolidine-4,5-diones of the formula II in the form of their disodium salts, these are first made anhydrous by sharp drying and then advantageously suspended also in a polar aprotic solvent. At least 2 moles preferably 2 to 2.2 moles, of a compound of the formula III are used per 1 mole of disodium salt of a compound of the formula II. The reaction can take place at temperatures between 20° and 180° C. Preferably the reaction is carried out in the temperature range between 60° and 140° C. The working up of the reaction takes place in the manner as described hereinbefore.

The imidazolidine-4,5-diones of the formula II are known compounds and can be obtained in accordance with German Offenlegungsschrift No. 2,018,433 by reacting dicyan with ketones in an aqueous alkaline medium. When using aldehydes, compounds of the formula II, in which each of $R^1$ and $R^2$ represents hydrogen, are obtained.

The chlorine and bromine compounds of the formula III, for example p-chloromethylbenzoic acid, chloroacetic acid, β-chloropropionic acid, α-chloropropionic acid, α- or β-bromobutyric acid, and others, are also known from the literature and are obtained, for example, by photochlorination, photobromination, or by addition of hydrogen bromide or hydrogen chloride to corresponding α,β-unsaturated compounds, such as acrylic acid, acrylonitrile, acrylic esters or acrylic chlorides, by known processes.

The dicarboxylic acids and dicarboxylic acid derivatives of the formula I, in which R represents phenylene, X represents nitrile, phenoxycarbonyl or alkoxycarbonyl containing 1 to 10 carbon atoms in the alkoxy moiety, $R^1$ represents a hydrogen atom and $R^2$ represents alkyl of 1 to 17 carbon atoms or cycloalkyl with 5 to 8 ring members, are obtained by the catalytic hydrogenation of a compound of the formula IV

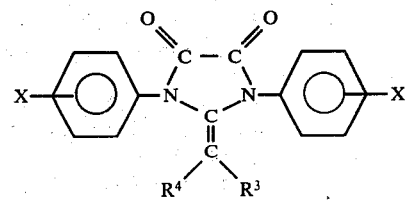

wherein X is as defined hereinbefore, $R^3$ represents hydrogen or alkyl of 1 to 17 carbon atoms, $R^4$ represents a hydrogen atom or $R^3$ and $R^4$ together represent alkylene of 4 to 7 carbon atoms. Preferably $R^3$ is alkyl of 1 to 3 carbon atoms and, in particular, hydrogen.

The reaction is normally carried out in solution using polar aprotic solvents, such as dimethyl formamide. Suitable catalysts are Raney nickel and noble metal catalysts, such as platinum or palladium. The isolation of the compounds of the present invention is effected by conventional methods. The compounds of the formula IV can be obtained as described in Beilstein, 24, page 339. The corresponding dicarboxylic acid chlorides can be obtained by chlorinating the dicarboxylic acids of the present invention with, for example, thionyl chloride, phosphorus trichloride or phosphorus pentachloride, by known methods. The esters of the present invention can be obtained from these dicarboxylic acid chlorides and from the dicarboxylic acids by esterification with phenol or alkanols.

The dicarboxylic acids and dicarboxylic acid derivatives of this invention are colourless crystalline substances which melt at temperatures between 50° and 350° C, are readily soluble in organic solvents but are insoluble, or only very sparingly soluble, in water, and have a surprisingly high heat resistance. They constitute useful monomers which are suitable for manufacturing heat-resistant plastics. Thus, for example, the dicarboxylic acids, the dicarboxylic acid halides and dicarboxylic acid diesters can be converted with diols into linear polyesters with very useful mechanical properties. The diglycidyl esters which are obtained from the dicarboxylic acids by glycidylation with epihalohydrin can also be cured to give epoxide resins with useful properties. The polyesters contain acid amide groups without hydrogen at the nitrogen atom. They are therefore characterised by a low hydrogen uptake.

The invention is described in more detail by the following Examples.

A. MANUFACTURING EXAMPLES

Example 1

1,3-bis-(4'-methoxycarbonylphenylmethyl)-2,2-dimethylimidazolidine-4,5-dione

In a 4-necked flask, equipped with stirrer, reflux cooler, thermometer and drip funnel, a solution of 110.8 g (0.6 mole) of p-chloromethylbenzoic acid methyl ester in 150 ml of hexamethylphosphoric triamide is added dropwise, with stirring, at 25° C to a solution (prepared at 5°–10° C) of 38.4 g (0.3 mole) of 2,2-dimethylimidazolidine-4,5-dione and 32.4 g (0.6 mole) of sodium methylate in 225 ml of anhydrous methanol and 225 ml of hexamethylphosphoric triamide.

When the addition is complete, the mixture is stirred for 2 hours at 80° C. After it has cooled to room temperature, the resultant brown suspension is poured, with vigorous stirring, into app. 2000 ml of ice water. The crystalline precipitate which has formed is filtered off after 1 hour, washed thoroughly with water and suction dried.

The crude product is recrystallised from 3000 ml of n-butanol and dried in vacuo (1 Torr) for 8 hours at 100° C. Yield: 38.4 g of a colourless crystalline product with a melting point of 242°–245° C.

The infra-red and nuclear magnetic resonance spectra of the compound confirm the presumed structure.

The elemental analysis yields the following results:

| calculated (for $C_{23}H_{24}N_2O_6$) | found |
| --- | --- |
| C 65.08% | C 65.2% |
| H 5.70% | H 5.8% |
| N 6.60% | N 6.8% |

EXAMPLE 2

1,3-bis-methoxycarbonylmethyl-2,2dimethylimidazolidine-4,5-dione

A solution of 12.8 g (0.1 mole) of 2,2-dimethylimidazolidine-4,5-dione in 70 ml of dimethyl formamide is slowly added dropwise, with stirring, at 20°–30° C to a suspension of 4.8 g (0.2 mole) of sodium hydride in 60 ml of dimethyl formamide. When the uptake of hydrogen has ceased, a solution of 33.4 g (0.2 mole) of bromacetic acid ethyl ester in 30 ml of dimethylformamide is added dropwise at 40°–50° C. After it has been stirred for 1 hour at 80° C, the reaction mixture is evaporated to dryness in vacuo. The residue is washed with ether and taken up in chloroform. The insoluble potassium bromide is filtered off and the chloroform solution evaporated. The residue is recrystallised from n-butanol to yield 7.8 g of colourless crystals with a melting point of 129°–130° C. The infra-red and nuclear magnetic resonance spectra confirm the presumed structure and the results of the elemental analysis are:

| calculated (for $C_{13}H_{20}N_2O_6$) | found |
| --- | --- |
| C 51.99% | C 52.0% |
| H 6.71% | H 6.7% |
| N 9.33% | N 9.3% |

Example 3

1,3-bis-(4'-methoxycarbonylphenylmethyl)-2,2-pentamethyleneimidazolidine-4,5-dione A solution of 47.1 g (0.28 mole) of 2,2-pentamethyleneimidazolidine-4,5-dione in 250 ml of dimethyl formamide is slowly added dropwise at 30°–40° C to a suspension of 13.4 g (0.56 mole) of sodium hydride in 800 ml of dimethyl formamide with stirring. When the uptake of hydrogen has ceased, a solution of 103.4 g (0.56 mole) of p-chloromethylbenzoic acid methyl ester in 100 ml of dimethylformamide is added dropwise at 50°–55° C.

After it has been stirred for 1 hour at 80° C, the reaction mixture is cooled to room temperature and poured into 7 liters of ice water with vigorous stirring. The precipitated product is dried and recrystallised from xylene. Colourless crystals with a melting point of 252°–256° C are obtained. The IR and NMR spectra confirm the presumed structure.

Elemental analysis:

| calculated (for $C_{26}H_{28}N_2O_6$) | found |
| --- | --- |
| C 67.23% | C 66.7% |
| H 6.08% | H 6.1% |
| N 6.03% | N 5.9% |

Example 4

1,3-bis-(4'-methoxycarbonylphenyl)-2-methylimidazolidine-4,5-dione

A solution of 40.8 g (0.1 mole) of 1,3-bis-(4'-methoxycarbonylphenyl)-2-methylene-imidazolidine-4,5-dione in 500 ml of dimethylformamide is hydrogenated in a laboratory hydrogenating apparatus, after addition of 2 g of a 5% palladium on charcoal catalyst, at room temperature and with vigorous stirring under slight hydrogen overpressure, until the uptake of hydrogen has ceased. The catalyst is filtered off and the solution is poured into 3 liters of ice water with vigorous stirring. The precipitated product is recrystallised from xylene, to yield 32 g of colourless crystals with a melting point of 250° C. The IR and NMR spectra confirm the presumed structure.

Elemental analysis:

| calculated (for $C_{22}H_{22}N_2O_6$) | found |
| --- | --- |
| C 64.38% | C 64.7% |
| H 5.40% | H 5.3% |
| N 6.83% | N 6.9% |

EXAMPLE 5

1,3-bis-(4'-butoxycarbonylphenylmethyl)-2,2-dimethylimidazolidine-4,5-dione 5 g (0.0118 mole) of 1,3-bis-(4'-methoxycarbonylphenylmethyl)-2,2-dimethylimidazolidine-4,5-dione, with the addition of 0.01% of titanium as titanium tetraisopropylate, are refluxed for 2 hours in n-butanol. The methanol which forms is distilled off continuously. The colourless crystals which precipitate after the reaction mixture has cooled are collected by suction filtration and recrystallised from n-butanol to yield 4.2 g of colourless crystals with a melting point of 111°–112° C. The IR and NMR spectra confirm the presumed structure.

Elemental analysis:

| calculated (for $C_{29}H_{36}N_2O_6$) | found |
| --- | --- |
| C 68.48% | C 68.5% |
| H 7.13% | H 7.1% |
| N 5.51% | N 5.6% |

Example 6

1,3-bis-(4'-carboxyphenylmethyl)-2,2-dimethylimidazolidine-4,5-dione 38.2 g (0.09 mole) of 1,3-bis-(4'-methoxycarbonylphenyl-2,2-dimethylimidazolidine-4,5-dione are dissolved in 300 ml of boiling ethanol. To this solution is added dropwise, with stirring, a solution of 10.1 g (0.18 mole) of KOH in ethanol. When the addition is complete, the reaction mixture is refluxed for 90 minutes and then cooled. The product which has recrystallised out in the process (potassium salt) is collected by suction filtration and dissolved in 400 ml of water. Addition of dilute hydrochloric acid causes a colourless crystalline product to precipitate which, after it has been suction dried, is recrystallised from dimethylformamide/water.

Yield: 30 g of colourless crystals with a melting point of 340° C (with decomp.).

The IR and NMR spectra confirm the presumed structure.

Elemental analysis:

| calculated ($C_{21}H_{20}N_2O_6$) | found |
|---|---|
| C 63.63% | C 63.5% |
| H 5.08% | H 5.2% |
| N 7.07% | N 7.2% |

Example 7

1,3-bis-(4'-chlorocarbonylphenylmethyl)-2,2-dimethylimidazolidine-4,5-dione 19.8 g (0.05 mole) of 1,3-bis-(4'-carboxyphenylmethyl)-2,2-dimethylimidazolidine-4,5-dione are refluxed in 70 ml of thionyl chloride until a solution is obtained. The reaction mixture is then evaporated to dryness in vacuo. The residue is recrystallised from dioxane under anhydrous conditions. Colourless crystals with a melting point of 232°-235° C are obtained.

Elemental analysis:

| calculated (for $C_{21}H_{18}Cl_2N_2O_4$) | found |
|---|---|
| Cl 16.36% | Cl 16.4% |

Example 8

1,3-bis-(4'-phenoxycarbonylphenylmethyl)-2,2-dimethylimidazolidine-4,5-dione

To a solution of 10 g (0.106 mole) of phenol in 20 ml of pyridine are added at room temperature, with stirring, 5 g (0.0115 mole) of 1,3-bis-(4'-chlorocarbonylphenylmethyl)-2,2-dimethylimidazolidine-4,5-dione.

After 1 hour the reaction mixture is poured into ice water. The precipitated oily product is separated and recrystallised repeatedly from dioxane. Colourless crystals with a melting point of 254°-260° C are obtained.

IR and NMR spectra confirm the presumed structure.

B. USE EXAMPLE

Example 9

Homopolyester with ethylene glycol 4.24 g of 1,3-bis-(4'-methoxycarbonylphenylmethyl)-2,2-dimethylimidazolidine-4,5-dione and 4.5 g of ethylene glycol are put into a 200 ml glass reactor equipped with stirrer, nitrogen inlet and cooler, and 0.01% of zinc (as acetate) and 0.03% of antimony (as antimony trioxide) are added thereto. The reaction mixture is heated in an oil bath to 200° C in the course of 40 minutes, then the temperature is raised to 240° C and kept thereat for 80 minutes. During this time 99% of the theoretical amount of methanol distills off.

The temperature of the oil bath is then adjusted to 260° C and after half an hour a vacuum of 0.05 Torr is carefully applied. After this vacuum has been attained, polycondensation is effected for 20 minutes with stirring, then nitrogen is introduced and the polyester is removed from the reactor. The relative viscosity of the homopolyester is 1.87 (1% solution in tetrachloroethane/phenol—1/1 measured at 30° C) and the glass transition temperature is 145° C measured in a differential scanning calorimeter 2B).

We claim:

1. A dicarboxylic acid or derivative which contains an imidazolidine-4, 5-dione ring, of the formula I

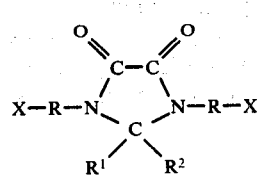

wherein

X represents nitrile, carboxyl, chlorocarbonyl, phenoxycarbonyl or alkoxycarbonyl of 1 to 10 carbon atoms in the alkoxy moiety, R represents alkylene of 1 or 2 carbon atoms in the chain, said alkylene substituted with alkyl groups of 1 to 6 carbon atoms, cyclohexylene, phenylene or benzylene the methyl group of which is attached to the nitrogen atom, each of $R^1$ and $R^2$ independently represents hydrogen, alkyl of 1 to 18 carbon atoms, cycloalkyl of 5 to 8 ring members, phenyl, or together $R^1$ and $R^2$ represent tetramethylene, pentamethylene, hexamethylene or heptamethylene, with the proviso that, if R represents phenylene, $R^1$ is a hydrogen atom and $R^2$ is alkyl of 1 to 18 carbon atoms or cycloalkyl of 5 to 8 ring members.

2. A dicarboxylic acid or derivative according to claim 1, wherein X represents carboxyl, phenoxycarbonyl, methoxy or ethoxycarbonyl.

3. A dicarboxylic acid or derivative according to claim 1, wherein R represents methylene, ethylidene, ethylene, 1,4-phenylene or 1,4-benzylene.

4. A dicarboxylic acid or derivative according to claims 1, wherein each of $R^1$ and $R^2$ independently represents hydrogen, alkyl of 1 to 6 carbon atoms, or together they represent tetramethylene or pentamethylene.

5. A dicarboxylic acid or derivative according to claim 4, wherein alkyl is methyl or ethyl.

6. 1,3-Bis-(4'-methoxycarbonylphenylmethyl)-2,2-dimethylimidazolidine-4,5-dione according to claim 1.

7. 1,3-Bis-(4'-methoxycarbonylphenyl)-2-methylimidazolidine-4,5-dione according to claim 1.

8. 1,3-Bis-methoxycarbonylmethyl-2,2-dimethylimidazolidine-4,5-dione according to claim 1.

9. 1,3-Bis-(4'-methoxycarbonylphenylmethyl)-2,2-pentamethyleneimidazolidine-4,5-dione according to claim 1.

10. 1,3-Bis-(4'-butoxycarbonylphenylmethyl)-2,2-dimethylimidazolidine-4,5-dione according to claim 1.

11. 1,3-Bis-(4'-carboxyphenylmethyl)-2,2-methylimidazolidine-4,5-dione according to claim 1.

12. 1,3-Bis-(4'chlorocarbonylphenylmethyl)-2,2-dimethylimidazolidine-4,5-dione according to claim 1.

13. 1,3-Bis-(4'-phenoxycarbonylphenylmethyl)-2,2-dimethylimidazolidine-4,5-dione according to claim 1.

* * * * *